(12) United States Patent
Sarathi et al.

(10) Patent No.: US 8,327,020 B1
(45) Date of Patent: Dec. 4, 2012

(54) SYSTEMS AND METHODS FOR HEALTHCARE TRANSACTION ROUTING WITH DESTINATION-BASED THROTTLING

(75) Inventors: Nikhil Sarathi, Cumming, GA (US); Marty Smith, Alpharetta, GA (US)

(73) Assignee: McKesson Financial Holdings Limited (BM)

( * ) Notice: Subject to any disclaimer, the term of this patent is extended or adjusted under 35 U.S.C. 154(b) by 246 days.

(21) Appl. No.: 12/893,546

(22) Filed: Sep. 29, 2010

(51) Int. Cl.
*G06F 15/173* (2006.01)
(52) U.S. Cl. ........................................ 709/239; 709/226
(58) Field of Classification Search .................. None
See application file for complete search history.

(56) References Cited

U.S. PATENT DOCUMENTS

| | | | |
|---|---|---|---|
| 5,892,818 A * | 4/1999 | Lee | 379/112.1 |
| 6,456,624 B1 * | 9/2002 | Eccles et al. | 370/400 |
| 2005/0288964 A1 * | 12/2005 | Lutzen et al. | 705/2 |
| 2012/0060062 A1 * | 3/2012 | Lin et al. | 714/48 |

* cited by examiner

*Primary Examiner* — John B. Walsh
(74) *Attorney, Agent, or Firm* — Sutherland Asbill & Brennan LLP

(57) ABSTRACT

Systems and methods are provided for transaction routing with destination-based throttling. The systems and methods may include receiving a healthcare transaction request from a source computer, where the healthcare transaction request includes at least a destination identifier that identifies a destination of the healthcare transaction request; identifying, based at least in part on the destination identifier, a current transaction count, the current transaction count indicating an extent to which one or more prior healthcare transaction requests remain unprocessed by the destination; comparing the identified current transaction count to at least one threshold value; and determining, based at least in part on the comparison, whether to deliver the healthcare transaction request to the destination.

16 Claims, 3 Drawing Sheets

SYSTEMS AND METHODS FOR HEALTHCARE TRANSACTION ROUTING WITH DESTINATION-BASED THROTTLING

FIELD OF THE INVENTION

Aspects of the invention relate generally to transaction routing, and more specifically to healthcare transaction routing with destination-based throttling.

BACKGROUND OF THE INVENTION

A service provider generally has a common input and output queue for receiving healthcare transactions from a source and routing healthcare transactions to a destination. The common queues are advantageous insofar as bandwidth can be allocated among different sources and destinations to balance loads as needs dynamically change among the different sources and destinations. However, common queues fail when one or more problematic healthcare transactions consume too much bandwidth to the detriment of otherwise non-problematic healthcare transactions. In such a situation, one or more problematic healthcare transactions can back up or stall a queue such that otherwise non-problematic healthcare transactions are rejected or otherwise not processed in a timely manner.

Thus, there is an opportunity for systems and methods for healthcare transaction routing with destination-based throttling.

SUMMARY OF THE INVENTION

Some or all of the above needs and/or problems may be addressed by certain embodiments of the invention. Embodiments of the invention may include systems and methods for healthcare transaction routing with destination-based throttling. In one embodiment, there is a computer-implemented method. The method may include: receiving a healthcare transaction request from a source computer, wherein the healthcare transaction request includes at least a destination identifier that identifies a destination of the healthcare transaction request; identifying, based at least in part on the destination identifier, a current transaction count, the current transaction count indicating an extent to which one or more prior healthcare transaction requests remain unprocessed by the destination; comparing the identified current transaction count to at least one threshold value; and determining, based at least in part on the comparison, whether to deliver the healthcare transaction request to the destination. One or more of the prior steps may be performed by one or more computers associated with a service provider.

In accordance with another embodiment of the invention, there is a system. The system may include at least one memory operable to store computer-executable instructions, and at least one processor configured to access the at least one memory. The at least one processor may be further configured to execute the computer-executable instructions to: receive a healthcare transaction request from a source computer, wherein the healthcare transaction request includes at least a destination identifier that identifies a destination of the healthcare transaction request; identify, based at least in part on the destination identifier, a current transaction count, the current transaction count indicating an extent to which one or more prior healthcare transaction requests remain unprocessed by the destination; compare the identified current transaction count to at least one threshold value; and determine, based at least in part on the comparison, whether to deliver the healthcare transaction request to the destination.

BRIEF DESCRIPTION OF THE DRAWINGS

Reference will now be made to the accompanying drawings, which are not necessarily drawn to scale, and wherein.

DETAILED DESCRIPTION

Example embodiments of invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

System Overview

Figure 1:
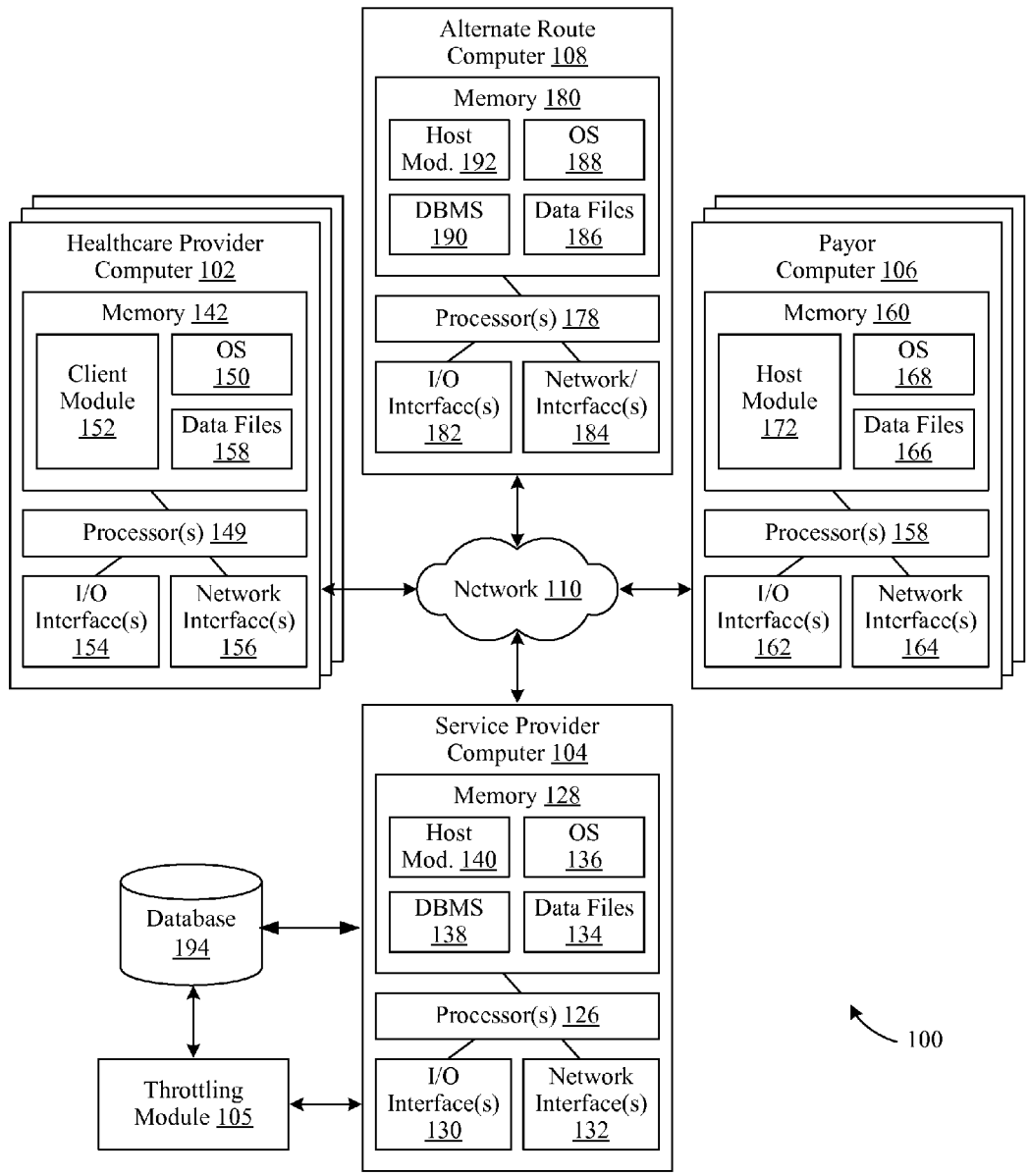
FIG. 1 illustrates an example healthcare system for supporting healthcare transaction routing with example destination-based throttling, according to an example embodiment of the invention.

FIG. 1 illustrates an example healthcare system 100 for supporting healthcare transaction routing with example destination-based throttling, according to an example embodiment of the invention. As shown in FIG. 1, the system 100 may include a healthcare provider computer 102, a service provider computer 104, a payor computer 106, and/or an alternate route computer 108, which are each configured for accessing and reading associated computer-readable media having stored thereon data and/or computer-executable instructions for implementing the various methods described herein. Generally, network devices and systems, including the one or more healthcare provider computers 102, service provider computers 104, payor computers 106, and alternate route computers 108 have hardware and/or software for transmitting and receiving data and/or computer-executable instructions over a communications link and at least one memory for storing data and/or computer-executable instructions. These network devices and systems may also include a processor for processing data and executing computer-executable instructions, as well as other internal and peripheral components that are well known in the art. As used herein, the term "computer-readable medium" may describe any form of computer memory or memory device.

As shown in FIG. 1, the healthcare provider computer 102, service provider computer 104, payor computer 106, and alternate route computer 108 may be in communication with each other via network 110, which as described below can include one or more separate or shared private and/or public networks, including the Internet. Each of these components—the healthcare provider computer 102, the service provider computer 104, the payor computer 106, the alternate route computer 108, and the network 110—will now be discussed in further detail.

First, the healthcare provider computer 102 may be associated with a pharmacy, a physician, a clinic/hospital, or yet another healthcare provider. The healthcare provider computer 102 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. In addition to having processor(s) 149, the healthcare provider computer 102 may further include a memory 142, input/output ("I/O") interface(s) 154, and network interface(s) 156. The memory 142 may be any computer-readable medium, coupled to the processor(s) 149, such as RAM, ROM, and/or a removable storage device for storing data files 158 and a database management system ("DBMS") to facilitate management of data files 158 and other data stored in the memory 142 and/or stored in separate databases. The memory 142 may store data files 158 and various program modules, such as an operating system ("OS") 150 and a client module 152. The OS 150 may be, but is not limited to, Microsoft Windows®, Apple OSX™, Linux, Unix, or a mainframe operating system. The client module 152 may be an Internet browser or other software, including a dedicated program, for interacting with the service provider computer 104.

For example, a user such as a physician, physician assistant, or other healthcare provider employee may utilize the client module 152 to initiate or direct a healthcare transaction request (e.g., eligibility request, claim status request, referral/preauthorization request, medical claim request, etc.) to the service provider computer 104 for routing to a payor computer 106 for processing, where the payor computer 106 may be a claims processor computer, or an insurance company computer, government-payor affiliated computer, third-party payor computer, and the like. Likewise, the client module 152 may be used to receive data and/or healthcare transaction responses from the service provider computer 104 or payor computer 106. Similarly, a user such as a pharmacist or pharmacy employee may utilize the client module 152 to initiate or direct a healthcare transaction request (e.g., eligibility request, claim status request, preauthorization request, prescription claim request, etc.) to the service provider computer 104 for routing to a payor computer 106 for processing, where the payor computer 106 may be a pharmacy benefits manager (PBM) computer, an insurance company computer, a government payor-affiliated computer, another third-party payor computer, or a claims processor computer, according to an example embodiment of the invention.

Second, the service provider computer 104 may include, but is not limited to, any processor-driven device that is configured for receiving, processing, and fulfilling requests and responses from the healthcare provider computer 102, the payor computer 106, and/or the alternate route computer 108 relating to healthcare transactions or other activities. The service provider computer 104 may include, but is not limited to, a server computer, a mainframe computer, one or more networked computers, or any other processor-based device. According to an example embodiment of the invention, the service provider computer 104 may comprise, but is not limited to, one or more "switches" or "switch providers" performing routing and processing (e.g., pre- and post-routing editing) of healthcare transactions between or among healthcare providers, pharmacies, payors/claims processors, and/or other service providers.

The service provider computer 104 may include processor(s) 126, a memory 128, input/output ("I/O") interface(s) 130, and network interface(s) 132. The memory 128 may be any computer-readable medium, coupled to the processor(s) 126, such as RAM, ROM, and/or a removable storage device for storing data files 134 and a database management system ("DBMS") 138 to facilitate management of data files 134 and other data stored in the memory 128 and/or stored in one or more databases 182. The data files 134 may also store routing tables for determining the destination of communications received from the healthcare provider computer 102, the payor computer 106, or the alternate route computer 108. The memory 128 may also store various program modules, such as an operating system ("OS") 136 and the host module 140. The OS 136 may be, but is not limited to, Microsoft Windows®, Apple OSX™, Linux, Unix, or a mainframe operating system. The host module 140 may receive, process, and respond to requests from the client module 152 of the healthcare provider computer 102, and may further receive, process, and respond to requests from the respective host modules 172, 192 of the payor computer 106 or the alternate route computer 108, respectively. In this regard, the memory 128 of the service provider computer 104 may also include one or more queues, including input queues to receive requests for processing and output queues providing results of processed requests.

A throttling module 105 may also be operative with the service provider computer 104. The throttling module 105 may include computer-executable instructions to support example transaction routing with destination-based throttling. The throttling module 105 may maintain a status of a particular destination identified by a healthcare transaction received from a source (e.g., a healthcare provider computer 104 or payor computer 106) such that a routing decision can be made regarding how to handle the received healthcare transaction. To support the foregoing status determination and routing decision, the throttling module 105 may maintain destination-specific information in memory 128 (e.g., data files 134) or the database 194. The destination-specific information may include, for a particular destination, one or more of the following information:

Destination ID: An identifier that identifies a particular destination (e.g., payor)

Current Transaction Count: May identify an extent to which one or more prior healthcare transaction requests remain unprocessed by the destination. For example, a Current Transaction Count can identify the number of healthcare transaction requests routed to the destination for which healthcare transaction responses are still pending (yet to be received from the destination), according to an example embodiment.

Maximum Threshold: Defines the maximum number of healthcare transaction requests that can remain unprocessed by the destination.

Alternate Route ID (Optional): Identification of an alternate route by which the destination can be reached. The identification of the alternate route can be any alphanumeric ID. For example, if an alternate route to the destination is available through another service provider computer, then the alternate route ID can identify the service provider (e.g., service provider name, service provider ID), along with any information needed to identify the destination (e.g., payor name, payor ID). In some example embodiments of the invention, the alternate route ID can utilize a bank identification number ("BIN") or a combination of a BIN and Processor Control Number ("PCN").

It will be appreciated that the destination-specific information can be stored in the memory 128 or the database 194 in a variety of formats, including one or more database objects, a file, a spreadsheet, and the like. Database 194 may be accessed by the service provider computer 104, the throttling module 105, or another affiliated entity, according to an example embodiment of the invention. According to an example embodiment of the invention, the storage of the destination-specific information may be stored in the memory 128 or another readily accessible cache, which may have faster retrieval than information stored in a database 194. Where destination-specific information is stored in the memory 128, it may be stored as a "singleton" object, where a different singleton object may be associated with a particular destination (e.g., Payor ID). In an example embodiment, the singleton object may be appropriate for maintaining destination specific information such as the Current Transaction Count because only a single instance of the singleton object may reside in the memory 128 for the particular destination, according to an example embodiment of the invention. As such, there would only be one globally accessible Current Transaction Count being maintained in the memory 128 or cache for a particular destination, according to an example embodiment of the invention. While a singleton object has been described herein, it will be appreciated that the destination-specific information may be stored in a variety of other objects or formats without departing from example embodiments of the invention.

The throttling module 105 may be implemented as computer-implemented instructions of the memory 128 of the service provider computer 104. Alternatively, the throttling module 105 may also be implemented as computer-implemented instructions of a memory of a separate processor-based system (e.g., having similar components as the service provider computer 104 or another computer), according to an example embodiment of the invention.

The payor computer 106 may associated with a claims processor, an insurance company, a pharmacy benefits manager ("PBM"), a government payor, a discount processor, or the like, according to an example embodiment of the invention. The payor computer 106 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The payor computer 106 may include processor(s) 158, a memory 160, input/output ("I/O") interface(s) 162, and network interface(s) 164. The memory 160 may be any computer-readable medium, coupled to the processor 158, such as RAM, ROM, and/or a removable storage device for storing data files 166 and a database management system ("DBMS") to facilitate management of data files 166 and other data stored in the memory 160 and/or stored in separate databases. The memory 160 may also store various program modules, such as an operating system ("OS") 168 and a host module 172. The OS 168 may be, but is not limited to, Microsoft Windows®, Apple OSX™, Linux, Unix, or a mainframe operating system. The host module 172 may receive, process, and respond to healthcare transaction requests from the client module 152 of the healthcare provider computer 102, and may further receive, process, and respond to healthcare transaction requests from the respective host modules 140, 192 of the service provider computer 104 or alternate route computer 108, respectively. According to an example embodiment of the invention, the payor computer 106 may be associated with coverage or benefits determined by a claims processor, an insurance company, a pharmacy benefits manager (PBM), a discount program, a government payor, or another third-party payor. According to an alternative example embodiment of the invention, a payor computer 106 may also be implemented as part of a service provider computer 104 (or the alternate route computer 108) or may otherwise be affiliated with the service provider computer 104 (or the alternate route computer 108).

The alternate route computer 108 may be another service provider computer similar to the service provider computer 104. In this regard, the alternate route computer 108 may include any processor-driven device that is configured for receiving, processing, and fulfilling requests and responses from the healthcare provider computer 102, the payor computer 106, and/or the service provider computer 104 relating to healthcare transactions or other activities. The alternate route computer 108 may include, but is not limited to, a server computer, a mainframe computer, one or more networked computers, or any other processor-based device. According to an example embodiment of the invention, the alternate route computer 108 may comprise, but is not limited to, one or more "switches" or "switch providers" performing routing and processing (e.g., pre- and post-routing editing) of healthcare transactions between or among healthcare providers, pharmacies, payors/claims processors, and/or other service providers.

The alternate route computer 108 may include a processor 178, a memory 180, input/output ("I/O") interface(s) 182, and a network interface 184. The memory 180 may be any computer-readable medium, coupled to the processor(s) 178, such as RAM, ROM, and/or a removable storage device for storing data files 186 and a database management system ("DBMS") 190 to facilitate management of data files 186 and other data stored in the memory 180 and/or stored in one or more separate databases. The data files 186 may also store routing tables for determining the destination of communications received from the healthcare provider computer 102, the payor computer 106, or the service provider computer 104. The memory 180 may also store various program modules, such as an operating system ("OS") 188 and the host module 192. The OS 188 may be, but is not limited to, Microsoft Windows®, Apple OSX™, Linux, Unix, or a mainframe operating system. The host module 192 may receive, process, and respond to requests from the client module 152 of the healthcare provider computer 102, and may further receive, process, and respond to requests from the respective host modules 172, 140 of the payor computer 106 or the service provider computer 104, respectively. In this regard, the memory 180 of the alternate route computer 108 may also include one or more queues, including input queues to receive requests for processing and output queues providing results of processed requests.

The network 110 may include any telecommunication and/or data network, whether public, private, or a combination thereof, including a local area network, a wide area network, an intranet, an internet, the Internet, intermediate hand-held data transfer devices, a publicly switched telephone network (PSTN), and/or any combination thereof and may be wired and/or wireless. The network 110 may also allow for real-time, off-line, and/or batch transactions to be transmitted between or among the healthcare provider computer 102, the service provider computer 104, the payor computer 106, and/or the alternate route computer 108. Due to network connectivity, various methodologies as described herein may be practiced in the context of distributed computing environments.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

It will also be appreciated that while database 194 is illustrated as being shared between the throttling module 105 and the service provider computer 104, the database 194 may be respective separate databases for each of the throttling module 105 and the service provider computer 194. Information may be transferred from one database to another on a periodic basis, on an as-needed basis, or on an as-requested basis, according to an example embodiment of the invention.

Operational Overview

Figure 2:
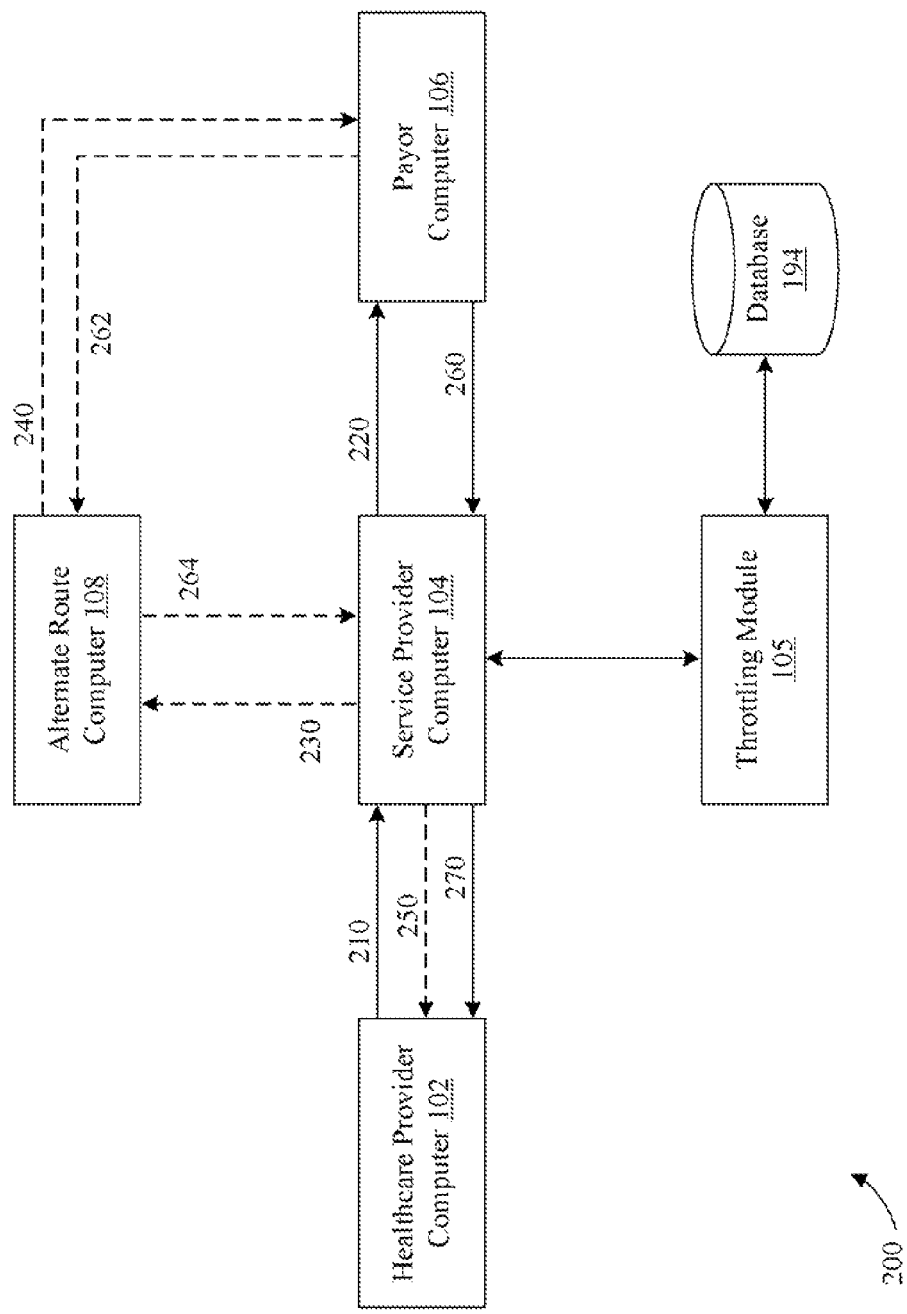
FIG. 2 illustrates an example block diagram for healthcare transaction routing in accordance with example destination-based throttling, according to an example embodiment of the invention.

FIG. 2 illustrates an example block diagram for healthcare transaction routing in accordance with example destination-based throttling, according to an example embodiment of the invention. The block diagram of FIG. 2 will be discussed in conjunction with the flow diagram of FIG. 3.

Figure 3:
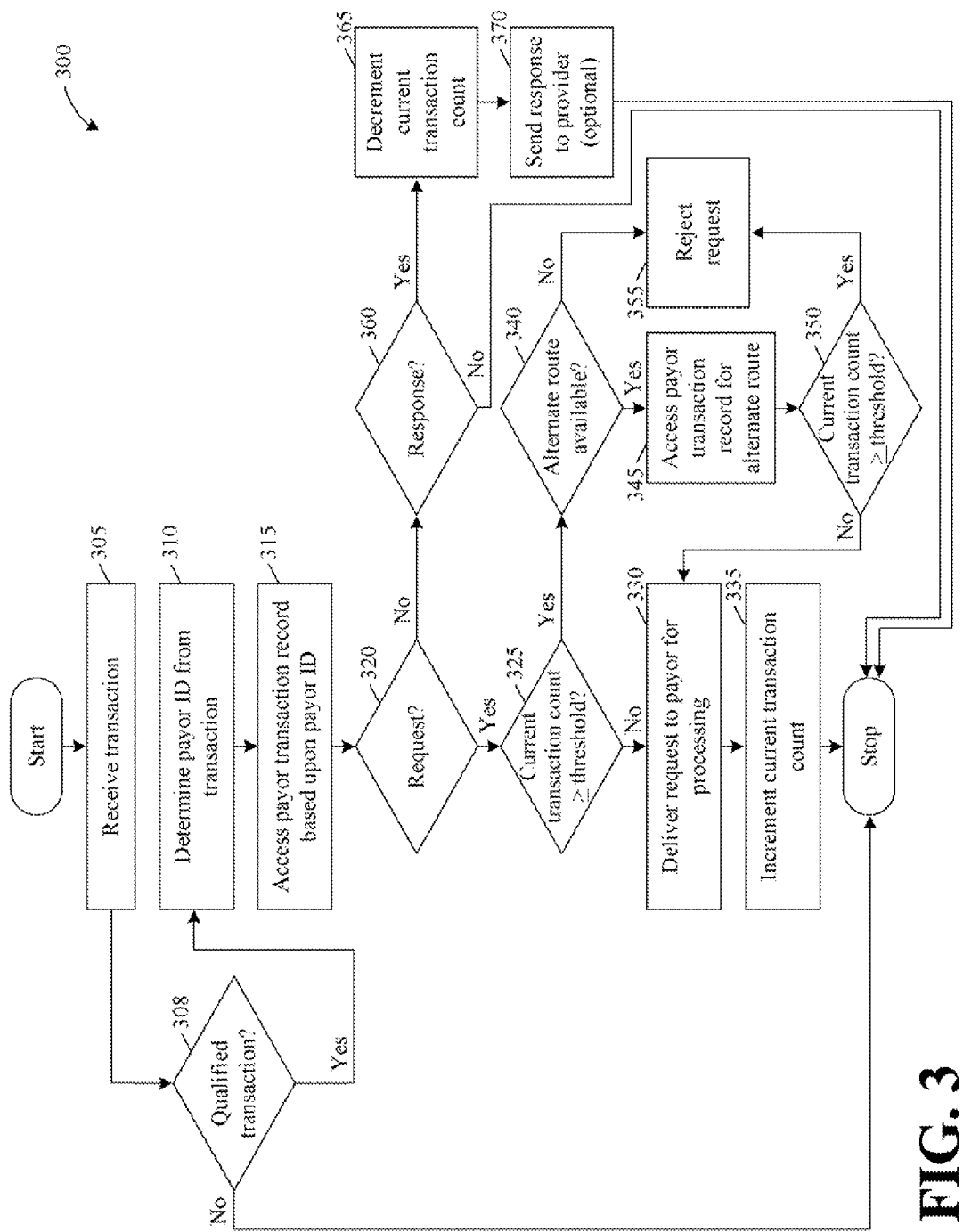
FIG. 3 illustrates an example flow diagram for healthcare transaction routing in accordance with example destination-based throttling, according to an example embodiment of the invention.

Referring now to FIGS. 2 and 3, in block 302, the service provider computer 104 may receive a healthcare transaction, which may take the form of a healthcare transaction request or a healthcare transaction response. In general, a healthcare transaction request may request processing or a service from the intended destination of the healthcare transaction request. Likewise, a healthcare transaction response may be generated by the destination (e.g., a payor computer 106) to indicate a result of processing the healthcare transaction request. The two sections below describe respective processing that may occur, depending upon whether a healthcare transaction request or a healthcare transaction response is received by the service provider computer 104.

1. Healthcare Transaction Request Received

According to an example embodiment, at block 305, the service provider computer 104 may receive a healthcare transaction request 210 from a source computer such as a healthcare provider computer 102. The healthcare transaction request 210 may be in accordance with an ANSI Electronic Data Interchange (EDI) format (e.g., ANSI X12 EDI), a version of an NCPDP Telecommunication Standard, although other standards may be utilized as well.

In an example embodiment of the invention, the healthcare provider computer 102 may be a physician/hospital/clinic computer such that the healthcare transaction request 210 may be a medical transaction request such as an eligibility request, a preauthorization request, a claim status request, etc. Alternatively, the healthcare provider computer 102 may be a pharmacy computer such that the healthcare transaction request 210 may be a pharmacy transaction request such as an eligibility request, preauthorization request, a claim status request, etc. Other healthcare transaction requests 210 may be available, including, but not limited to, pharmacy claim requests or medical claim requests, or any other type of professional or institutional claims, according to an example embodiment of the invention.

It will be appreciated that an eligibility request may be used to verify whether a particular patient has coverage with a particular payor (e.g., insurance company, PBM, etc.). A preauthorization request may be used to request advance authorization of coverage from a payor for a service or drug/product to be provided by a healthcare provider (e.g., doctor/clinic/hospital, pharmacy, etc.) to a patient. A claim status request may be used to verify a status (e.g., paid, rejected, in process, suspended, etc.) of a claim request previously provided by a healthcare provider to a particular payor. Likewise, a healthcare claim request may be a request for reimbursement from a payor for a service or drug/product provided to a patient.

The received healthcare transaction request 210 may include information identifying a source/originator of the healthcare transaction request 210 and a destination to process the healthcare transaction request 210. The source/originator identifier may be in the form of a Healthcare Provider Identifier while the destination identifier may be in the form of a Payor Identifier that identifies a particular payor (e.g., claims processor, insurance company, government payor, pharmacy benefits manager, etc.). In an alternative embodiment of the invention, the source identifier could also be the Payor Identifier while the destination identifier could be the Healthcare provider identifier, if for example, the payor computer 106 were to originate a healthcare transaction request for processing by a healthcare provider computer 102. In an example embodiment, the source identifier and destination identifier can be a name of the entity (e.g., healthcare provider name and payor name, respectively), another identifier such as a National Provider Identifier (NPI) code, or a combination thereof. It will be appreciated that variations of the source and destination identifiers are available. For example, for claim transactions, the destination identifier can be in the form of a bank identification number (BIN) or a combination of a BIN/Processor Control Number (PCN) that identifies a particular payor, according to an example embodiment of the invention. Further, while a BIN or BIN/PCN combination can be included as a destination identifier for purposes of routing, other portions of the healthcare transaction request 210 could still include a National Provider Identifier (NPI), a Pharmacy ID, a Physician/Hospital/Clinic ID, etc. for use in processing by the final destination.

The healthcare transaction request 210 can also include a variety of additional information depending on the type of request 210, which may include one or more of patient information, insurance/coverage information, prescriber information, healthcare provider information, and/or date of service. As an example, an eligibility request can include at least patient information, insurance/coverage information, and healthcare provider information. A preauthorization request can include at least patient information, insurance/coverage information, healthcare provider information, and identification of a drug/product or service to be provided by the healthcare provider. A claim status request can include at least patient information, insurance/coverage information, healthcare provider information, and claim information (e.g., identification of drug/product or service provided). Examples of information included in the healthcare transaction request 210 may include, but are not limited to, one or more of the following:

Routing Information
   a. A routing identifier that identifies a destination of the healthcare transaction request 210. For example, a BIN or BIN/PCN can be used to identify a payor computer 106 (e.g., a PBM, a claims processor, insurance company, etc.) as a destination of the request 210.

Patient Information
   a. Patient First Name
   b. Patient Last Name
   c. Gender Code
   d. Patient Street Address
   e. Patient City Address
   f. Patient State/Province Address
   g. Patient ZIP/Postal Zone
   h. Patient Phone Number
   i. Patient ID or other identifier
   j. Patient E-mail Address Insurance/Coverage Information
  a. Cardholder Name (e.g., Cardholder First Name, Cardholder Last Name)
  b. Cardholder ID or other identifier (e.g., Cardholder ID and Group ID)
Healthcare Provider Information
  Healthcare Provider/Prescriber Information
  a. Provider ID or other identifier (e.g. National Provider Identifier (NPI), Drug Enforcement Administration (DEA) number, state-issued identification, etc.)
  b. Provider Last Name
  c. Provider Contact Information (e.g., Telephone Number)
  Pharmacy Provider Information
  a. Service Provider ID (e.g., NCPDP Provider ID, NPI code, etc.)
Claim Information
  a. Product/Service ID (e.g., National Drug Code (NDC) for drugs, Universal Product Code (UPC) for products, or other code sets for Services)
  b. Date Prescription Written, Quantity Dispensed, Days Supply, Pricing information for the drug or product (for prescription claims)
  c. Diagnosis/Condition
Date of Service.

It will be appreciated that additional or alternative information can be included in a healthcare transaction request 210 depending upon the type of the healthcare transaction request 210, according to an example embodiment of the invention.

Having received a healthcare transaction request 210 at block 305, processing may proceed to block 308. At block 308, the service provider 104 may determine whether the healthcare transaction request 210 is of an eligible type, such that the throttling module 105 may be utilized to provide example destination-based throttling services described herein. For example, in an example embodiment of the invention, synchronous, real-time communications with a destination may be managed by the throttling module 105 in accordance with destination-based throttling since synchronous, real-time communications have the potential to consume significant bandwidth and resources of the service provider computer 104. Indeed, with synchronous communications, the service provider computer 104 communicates a healthcare transaction request to the destination (e.g., payor computer 106) and awaits a response from the destination; accordingly, if a response is not received in a timely manner, then resources and bandwidth of the service provider computer 104 may be consumed while waiting for the response or a time-out to occur. In an example embodiment of the invention, a healthcare transaction request 210 in the form of an eligibility request, a preauthorization request, or claim status request may be an eligible type in accordance with block 308.

If block 308 determines that the healthcare transaction is of an eligible type, then processing may proceed with block 310. At block 310, the service provider computer 104 may provide a copy of the healthcare transaction request 210, or at least a portion of the healthcare transaction request 210 to the throttling module 105 for further processing. At block 310, the throttling module 105 and/or service provider computer 104 will determine the destination ID (e.g., Payor ID, Payor Name, etc.) from the healthcare transaction request 210. At block 315, the throttling module 105 and/or service provider computer 104 may utilize the destination ID from the healthcare transaction request 210 to locate the corresponding destination-specific information/record in the memory 128, database 194, or another storage location. The destination-specific information/record may include a Current Transaction Count, a Maximum Threshold, and any Alternate Route ID that is associated with a particular destination ID.

Following block 315 is block 320. Block 320 determines whether the received healthcare transaction is in the form of a request or a response. Since healthcare transaction request 210 is a "request", processing may proceed to block 325. Block 325 determines whether the intended destination of the healthcare transaction request 210 is offline, non-responsive, or otherwise not processing healthcare transaction requests in a timely manner. To do so, block 325 may compare the Current Transaction Count with the Maximum Threshold (values were obtained from block 315). As an example, if the Current Transaction Count is less than the Maximum Threshold at block 325, then the throttling module 105 and/or service provider computer 104 may determine that the intended destination of the healthcare transaction request 210 is functioning properly such that the healthcare transaction request 210 can be routed to its requested destination. In this case, processing may proceed to block 330. At block 330, the service provider computer 104 may deliver a copy of the healthcare transaction request 210, or at least a portion of information in the healthcare transaction request 210, in a healthcare transaction request 220 to the payor computer 106 (corresponding to the destination of the healthcare transaction request 210). At block 335, the throttling module 105 and/or service provider computer 104 may update the Current Transaction Count in the destination-specific information/record of the memory 128 (e.g., singleton object) or database 194 to reflect that one additional healthcare transaction request (e.g., request 210) has been delivered to the destination (e.g., payor computer 106). For example, the Current Transaction Count can be incremented by a predetermined amount (e.g., by 1 or another amount), depending upon how the Maximum Threshold is set and how the comparison is being performed at block 325.

On the other hand, block 325 may determine that the destination is offline, non-responsive, or otherwise not processing healthcare transaction requests in a timely manner. For example, block 325 may have determined that the Current Transaction Count is equal to or exceeds the Maximum Threshold. In this case, the throttling module 105 and/or the service provider computer 104 may determine that the healthcare transaction request 220 cannot be delivered directly to the payor computer 106 corresponding to the intended destination, and processing may proceed to block 340. At block 340, the throttling module 105 and/or service provider computer 104 may determine whether the destination-specific information/record may optionally include an Alternate Route ID that identifies an alternative path to the intended destination. If an Alternate Route ID exists at block 340, then processing may proceed to block 345. At block 340, the throttling module 105 and/or service provider computer 104 may utilize the Alternate Route ID as another destination ID to locate the corresponding destination-specific information/record in the memory 128, database 194, or other storage location. In other words, the Alternate Route ID may be treated as an alternate destination in which a corresponding destination-specific information/record may be located. The destination-specific information/record may include a Current Transaction Count, a Maximum Threshold, and optionally any Alternate Route ID that is applicable to the alternate destination. Following block 345, processing may proceed to block 350. Block 350 may determine whether the alternate destination is offline, non-responsive, or otherwise not processing healthcare transaction requests in a timely manner. To do so, block 350 may compare the Current Transaction Count with the Maximum Threshold associated with the alternate route (values were obtained from block 345). As an example, if the Current Transaction Count is less than the Maximum Threshold at block 350, then the throttling module 105 and/or service provider computer 104 may determine that the alternate route destination is functioning properly such that the healthcare transaction request 210 can be routed through the alternate route destination to the original intended destination of healthcare transaction request 210. In this case, processing may proceed to block 330, where the service provider computer 104 may deliver a copy of the healthcare transaction request 210, or at least a portion of the information in the healthcare transaction request 210, in a healthcare transaction request 230, to the alternate route computer 108 (corresponding to the alternate route ID). The alternate route computer 108 may then deliver the healthcare transaction request 230, or at least a portion of information in the healthcare transaction request 230, as a healthcare transaction request 240 to the payor computer 106.

On the other hand, block 340 may determine that the alternate route destination is also offline, non-responsive, or otherwise not processing healthcare transaction requests in a timely manner. For example, block 340 may have determined that the Current Transaction Count is equal to or exceeds the Maximum Threshold. In this case, the throttling module 105 and/or the service provider computer 104 may determine that the healthcare transaction request 210 cannot be delivered to the alternate route computer 108 corresponding to the alternate route ID destination, and processing may proceed to block 355. At block 355, the service provider computer 104 may send a healthcare transaction response 250 in the form of a rejection or time-out response. The rejection or time-out response may indicate that the requested destination is unavailable or unresponsive such that the healthcare transaction response 250 could not be processed by the payor computer 106. In this way, the service provider computer 104 can preemptively send a rejection or time-out response to the healthcare provider computer 102 without routing a healthcare transaction request to the payor computer 106 and consuming processing time and resources to eventually receive a time-out response or significantly delayed response from the payor computer 106. In this way, the service provider computer 104 can retain processing time and resources to process and route healthcare transaction requests to other destinations (e.g., payors) that are operating properly.

2. Healthcare Transaction Response Received

According to an example embodiment, at block 305, the service provider computer 104 may receive a healthcare transaction response. For example, a healthcare transaction response 260 may be received by the service provider computer 104 directly from the payor computer 106. The healthcare transaction response 260 may indicate a result of processing the healthcare transaction request 220. In addition, the healthcare transaction response 260 may include similar information as that provided for the corresponding healthcare transaction request to which it pertains. Likewise, the healthcare transaction response 260 may also include identifying information to identify which particular healthcare transaction request is being responded to by the present response 260, according to an example embodiment of the invention.

Following block 305 is block 308. At block 308, the service provider 104 may determine whether the received healthcare transaction response 260 or is of an eligible type, such that the throttling module 105 may be utilized to provide example destination-based throttling services described herein. A healthcare transaction response 260 corresponding to a response for an eligibility request, a preauthorization request, or claim status request may be an eligible type in accordance with block 308. If block 308 determines that the healthcare transaction response 260 is of an eligible type, then processing may proceed with block 310.

At block 310, the service provider computer 104 may provide a copy of the healthcare transaction response 260, or at least a portion of the healthcare transaction response 260 to the throttling module 105 for further processing. At block 310, the throttling module 105 and/or service provider computer 104 will determine the destination ID (e.g., Payor ID, Payor Name, etc.) from the healthcare transaction response 260. It will be appreciated that the destination ID of a healthcare transaction response 260 may not refer to the destination of the healthcare transaction response, but instead the destination that processed the healthcare transaction request to which the healthcare transaction response 220 corresponds. At block 315, the throttling module 105 and/or service provider computer 104 may utilize the destination ID from the healthcare transaction response 260 to locate the corresponding destination-specific information/record in the memory 128, database 194, or another storage location. The destination-specific information/record may include a Current Transaction Count, a Maximum Threshold, and any Alternate Route ID that is associated with a particular destination ID.

Following block 315 is 320. Block 320 determines whether the received healthcare transaction is in the form of a request or a response. Since healthcare transaction response 260 is not a "request", processing may proceed to block 360. Block 360 may then determine whether the healthcare transaction response 260 corresponds to a "response" for a previously delivered healthcare transaction request 210, and if so, processing proceeds to block 365. At block 365, the throttling module 105 and/or service provider computer 104 may update the Current Transaction Count in the destination-specific information/record of the memory 128 or database 194 to reflect that a response has been received for a previously delivered healthcare transaction request. In other words, the Current Transaction Count is updated to reflect that one less healthcare transaction request remains unprocessed by the destination. For example, the Current Transaction Count can be decremented by a predetermined amount (e.g., by 1 or another amount), depending upon how the Maximum Threshold is set and how the comparison is being performed at block 325.

Following block 365 is block 370. At block 370, the service provider computer 104 can optionally deliver a copy of the healthcare transaction response 260, or at least a portion of the information in the healthcare transaction response 260, as a healthcare transaction response 270 to the healthcare provider computer 102.

In an alternative embodiment of the invention, the service provider computer may instead receive at block 305 a healthcare transaction response 264 from the alternate route computer 108 instead of from the payor computer 106. The transaction response 264 may be based upon a transaction response 262 received by the alternate route computer 108 from the payor computer 106. The healthcare transaction response 264 may indicate a result of processing (ultimately by payor computer 106) the healthcare transaction request 230. In such a case, similar processing as described above for healthcare transaction response 260 may occur. However, at block 365, processing may be different and the Current Transaction Count for a different destination-specific information/record may be updated. Indeed, the destination-specific information/record may be that corresponding to the alternate route ID, according to an example embodiment of the invention.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

It will be appreciated that each of the memories and data storage devices described herein can store data and information for subsequent retrieval. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices.

It will also be appreciated that each of the I/O interfaces described herein may facilitate communication between a processor and various I/O devices, such as a keyboard, mouse, printer, microphone, speaker, monitor, bar code readers/scanners, RFID readers, and the like. Likewise, each of the network interfaces described herein may take any of a number of forms, such as a network interface card, a modem, a wireless network card, and the like.

It will further be appreciated that while certain computers have been illustrated herein as a single computer or processor, the illustrated computers may actually be comprised of a group of computers or processors, according to an example embodiment of the invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
   receiving a healthcare transaction request from a source computer, wherein the healthcare transaction request includes at least a first destination identifier that identifies a destination of the healthcare transaction request;
   identifying, based at least in part on the first destination identifier, a first current transaction count, the first current transaction count indicating an extent to which one or more prior healthcare transaction requests remain unprocessed by the destination;
   comparing the identified first current transaction count to at least one first threshold value;
   determining, based at least in part on the comparison, whether to deliver the healthcare transaction request to the destination;
   responsive to a determination to not deliver the healthcare transaction request to the destination, determining, based at least in part on the first destination identifier, that an alternate route computer is available to provide an alternate route to the destination, the alternate route computer associated with a second destination identifier;
   identifying, based at least in part on the second destination identifier, a second current transaction count, the second current transaction count indicating an extent to which one or more prior healthcare transaction requests remain unprocessed by the alternate route computer;
   comparing the identified second current transaction count to at least one second threshold value; and
   determining, based at least in part on the comparison involving the second current transaction count, whether to deliver the healthcare transaction request to the alternate route computer for indirect delivery to the destination;
   responsive to a determination to deliver the healthcare transaction request to the alternate route computer, delivering the healthcare transaction request to the alternate route computer; and
   modifying the second current transaction count to reflect at least one additional healthcare transaction request that remains unprocessed by the alternate route computer,
   wherein the prior steps are performed by one or more computers associated with a service provider.

2. The computer-implemented method of claim 1, wherein a determination is made to deliver the healthcare transaction request to the destination, and further comprising:

delivering the healthcare transaction request to a destination computer associated with the destination, and modifying the first current transaction count to reflect at least one additional healthcare transaction request that remains unprocessed by the destination, wherein the prior steps are performed by one or more computers associated with the service provider.

3. The computer-implemented method of claim 2, wherein modifying the first current transaction count includes incrementing the first current transaction count.

4. The computer-implemented method of claim 2, further comprising:

receiving, from the destination computer, a healthcare transaction response associated with the healthcare transaction request, the healthcare transaction response indicating a result of processing the healthcare transaction request by the destination computer; and modifying the first current transaction count to reflect at least one less healthcare transaction request that remains unprocessed by the destination, wherein the prior steps are performed by one or more computers associated with the service provider.

5. The computer-implemented method of claim 1, wherein a determination is made to not deliver the healthcare transaction request to the destination, wherein the healthcare transaction request is not delivered to the destination, and further comprising:

delivering a healthcare transaction response to the source computer, the healthcare transaction response indicating that the healthcare transaction request was not delivered to the destination, wherein the prior step is performed by one or more computers associated with the service provider.

6. The computer-implemented method of claim 5, wherein the healthcare transaction response is in a form of a rejection response or a timed-out response.

7. The computer-implemented method of claim 1, wherein the source computer is associated with a healthcare provider, wherein the destination is associated with a payor, and wherein the healthcare transaction request is associated with an eligibility request, a preauthorization request, a claim status request, or a claim request.

8. The computer-implemented method of claim 1, wherein the first current transaction count is incremented when a healthcare transaction request is delivered to the destination, and wherein the first current transaction count is decremented when a healthcare transaction response is received from the destination.

9. A system, comprising:

at least one memory for storing computer-executable instructions; and at least one processor in communication with the at least one memory, wherein the at least one processor is configured to execute the computer-executable instructions to:

receive a healthcare transaction request from a source computer, wherein the healthcare transaction request includes at least a first destination identifier that identifies a destination of the healthcare transaction request;

identify, based at least in part on the first destination identifier, a first current transaction count, the first current transaction count indicating an extent to which one or more prior healthcare transaction requests remain unprocessed by the destination;

compare the identified first current transaction count to at least one first threshold value;

determine, based at least in part on the comparison, whether to deliver the healthcare transaction request to the destination;

responsive to a determination to not deliver the healthcare transaction request to the destination, determine, based at least in part on the first destination identifier, that an alternate route computer is available to provide an alternate route to the destination, the alternate route computer associated with a second destination identifier;

identify, based at least in part on the second destination identifier, a second current transaction count, the second current transaction count indicating an extent to which one or more prior healthcare transaction requests remain unprocessed by the alternate route computer;

compare the identified second current transaction count to at least one second threshold value;

determine, based at least in part on the comparison involving the second current transaction count, whether to deliver the healthcare transaction request to the alternate route computer for indirect delivery to the destination;

responsive to a determination to deliver the healthcare transaction request to the alternate route computer, deliver the healthcare transaction request to the alternate route computer; and modify the second current transaction count to reflect at least one additional healthcare transaction request that remains unprocessed by the alternate route computer.

10. The system of claim 9, wherein a determination is made to deliver the healthcare transaction request to the destination, and wherein the at least one processor is further configured to execute the computer-executable instructions to:

deliver the healthcare transaction request to a destination computer associated with the destination, and modify the first current transaction count to reflect at least one additional healthcare transaction request that remains unprocessed by the destination.

11. The system of claim 10, wherein the first current transaction count is modified by incrementing the first current transaction count.

12. The system of claim 10, wherein the at least one processor is further configured to execute the computer-executable instructions to:

receive, from the destination computer, a healthcare transaction response associated with the healthcare transaction request, the healthcare transaction response indicating a result of processing the healthcare transaction request by the destination computer; and modify the first current transaction count to reflect at least one less healthcare transaction request that remains unprocessed by the destination.

13. The system of claim 9, wherein a determination is made to not deliver the healthcare transaction request to the destination, wherein the healthcare transaction request is not delivered to the destination, and wherein the at least one processor is further configured to execute the computer-executable instructions to:

deliver a healthcare transaction response to the source computer, the healthcare transaction response indicating that the healthcare transaction request was not delivered to the destination.

14. The system of claim 13, wherein the healthcare transaction response is in a form of a rejection response or a timed-out response.

15. The system of claim 9, wherein the source computer is associated with a healthcare provider, wherein the destination is associated with a payor, and wherein the healthcare transaction request is associated with an eligibility request, a pre-authorization request, a claim status request, or a claim request.

16. The system of claim 9, wherein the current transaction count is stored in the at least one memory in association with the first destination identifier or another identifier associated with the first destination identifier, wherein the first current transaction count is incremented when a healthcare transaction request is delivered to the destination, and wherein the first current transaction count is decremented when a healthcare transaction response is received from the destination.

* * * * *